United States Patent
Greenwood et al.

(10) Patent No.: US 11,078,096 B2
(45) Date of Patent: Aug. 3, 2021

(54) SENSOR WITH MEMORY STORING CALIBRATION INFORMATION

(71) Applicant: Digital Concepts of Missouri, Inc., Maryland Heights, MO (US)

(72) Inventors: Jack Greenwood, St. Peters, MO (US); Christopher Seay Green, Affton, MO (US); Kenneth W. Law, St. Charles, MO (US)

(73) Assignee: Digital Concepts of Missouri, Inc., Maryland Heights, MO (US)

( * ) Notice: Subject to any disclaimer, the term of this patent is extended or adjusted under 35 U.S.C. 154(b) by 58 days.

(21) Appl. No.: 16/450,249

(22) Filed: Jun. 24, 2019

(65) Prior Publication Data

US 2019/0322556 A1 Oct. 24, 2019

Related U.S. Application Data

(62) Division of application No. 15/091,679, filed on Apr. 6, 2016, now Pat. No. 10,329,177.

(60) Provisional application No. 62/144,439, filed on Apr. 8, 2015.

(51) Int. Cl.
| | |
|---|---|
| *C02F 1/66* | (2006.01) |
| *G01N 27/416* | (2006.01) |
| *C02F 1/76* | (2006.01) |
| *C02F 103/42* | (2006.01) |
| *G01N 33/18* | (2006.01) |

(52) U.S. Cl.
CPC ............... *C02F 1/66* (2013.01); *C02F 1/76* (2013.01); *G01N 27/4163* (2013.01); *G01N 27/4166* (2013.01); *C02F 2103/42* (2013.01); *C02F 2209/005* (2013.01); *C02F 2209/02* (2013.01); *C02F 2209/04* (2013.01); *C02F 2209/06* (2013.01); *C02F 2209/10* (2013.01); *C02F 2209/29* (2013.01); *C02F 2209/42* (2013.01); *C02F 2303/04* (2013.01); *G01N 27/4165* (2013.01); *G01N 27/4167* (2013.01); *G01N 27/4168* (2013.01); *G01N 33/182* (2013.01)

(58) Field of Classification Search
None
See application file for complete search history.

(56) References Cited

U.S. PATENT DOCUMENTS

| | | | |
|---|---|---|---|
| 6,125,481 | A | 10/2000 | Sicilano |
| 6,272,446 | B1 | 8/2001 | Baekke et al. |
| 7,062,975 | B2 | 6/2006 | Schmid et al. |
| 7,551,275 | B2 | 6/2009 | Bonino et al. |

(Continued)

FOREIGN PATENT DOCUMENTS

EP 0 351 516 A2 1/1990

OTHER PUBLICATIONS

Chemtrac, Free Chlorine Probe Operations Manual dated Mar. 30, 2011, 28 pages.

(Continued)

*Primary Examiner* — Richard C Gurtowski
(74) *Attorney, Agent, or Firm* — Stinson LLP

(57) ABSTRACT

A sensor is configured to sense a parameter of an aqueous liquid. The sensor has an analog output port configured to provide an analog signal indicative of a sensed parameter, and a calibration memory device storing individual digital information indicative of a calibration of the sensor. A digital output port provides a digital signal indicative of the digital information. A treatment system and method is matched to the sensor.

10 Claims, 9 Drawing Sheets

(56) References Cited

U.S. PATENT DOCUMENTS

| | | |
|---|---|---|
| 8,324,824 B2 | 12/2012 | Lin et al. |
| 8,574,413 B2 | 11/2013 | Mosley et al. |
| 2002/0014410 A1 | 2/2002 | Silveri et al. |
| 2004/0124253 A1 | 7/2004 | Bergwin et al. |
| 2005/0139530 A1 | 6/2005 | Heiss |
| 2006/0060512 A1 | 3/2006 | Astle et al. |
| 2006/0106561 A1 | 5/2006 | Thiesen |
| 2007/0078608 A1 | 4/2007 | Broy |
| 2007/0126794 A1 | 6/2007 | Schick et al. |

OTHER PUBLICATIONS

Maxim Integrated Products, Inc., Minimal Remote 1-Wire Master Protocol—Application Note—Maxim (Mar. 3, 2004) 35 pages.
Maxim Integrated, Data Sheet 2431, 1024-Bit, 1-Wire EEPROM, www.maximintegrated.com, (2014), 27 pages.
Partial European Search Report for related application EP16164301.0 dated Nov. 18, 2016, 8 pages.

SENSOR WITH MEMORY STORING CALIBRATION INFORMATION

CROSS-REFERENCE TO RELATED APPLICATIONS

This application is a division of U.S. patent application Ser. No. 15/091,679, filed Apr. 6, 2016, now U.S. Pat. No. 10,329,177, which claims the benefit of U.S. Provisional Application No. 62/144,439, filed Apr. 8, 2015, the entire disclosures of which are incorporated herein by reference for all purposes.

BACKGROUND

The present invention relates to electrochemical probes, and more particularly to electrochemical sensors for measuring certain characteristics of liquids, particularly aqueous liquids, and components of such sensors.

In many situations, it is desirable to monitor a variety of water quality parameters, often at frequent intervals or even continuously. Water quality parameters include, for example, temperature, pH, free chlorine, total alkalinity, hardness, total dissolved solids, and oxidation reduction potential (ORP). Many of these parameters can be measured electrolytically. For ease of explanation, much of the following discussion will be with reference to monitoring water quality in a swimming pool, although it should be borne in mind that the discussion is likewise applicable to monitoring water quality in other settings, such as a spa, Jacuzzi™, hot tub, fountain, aquarium, sprinkler system to spray produce, water tank, or cooling tower.

Swimming pool water must be monitored vigilantly to ensure that the water is clean and safe for use. Conventionally, this is a manual process carried out by the owner or other caretaker of the pool. The process involves going to the pool with vials and chemicals, scooping water into vials, shaking the vials, and comparing the color of the resulting solutions to those on charts to determine the chemicals needed to restore proper pool chemistry. After testing, it is necessary to obtain the chemicals, measure them out, and add them to the pool water. For example, the chlorine disinfectant used to sanitize the pool may have been depleted by a heavy bather load, and more chlorine needed to destroy algae, waterborne germs, and oxidize organic debris introduced into the pool water by swimmers. It is a cumbersome process, and if pool water quality is not maintained properly, the swimmer can contract waterborne illnesses such as diarrhea, swimmer's ear, and skin infections.

The maintenance of swimming pool water is multifaceted in the number of factors that must be controlled. Scheme A shows water quality parameters recommended for swimming pool water.

| Scheme A | |
|---|---|
| Water Quality Parameter | Ideal Level |
| pH | 7.2 to 7.8 |
| Free Chlorine | 1.0 to 3.0 ppm |
| Total Alkalinity (buffering capacity) | 80 to 120 ppm |
| Salt | 2,700 to 3,400 ppm |
| Stabilizer | 60 to 80 ppm |
| Hardness | 200 to 400 ppm |
| Total Dissolved Solids | Less than 6,000 ppm |
| Oxidation-Reduction Potential | 650 mV |

Two critical factors in maintaining water balance are pH and free chlorine level (FCL). pH is a measurement of the concentration of hydrogen ions in water. It is measured using a logarithmic scale from 0 to 14, with pH 7 being neutral. For pool water to be in balance, the pH must be maintained at a level between 7.2 and 7.8. At pH below 7.2, the water is considered to be corrosive and can etch plaster and metal in equipment such as heat exchangers. Maintaining the pH higher than 7.8 will increase the tendency to form scale or cloudy water due to precipitation of calcium dissolved in the water. Higher pH will also render chlorine sanitizers ineffective, as discussed further below.

Addition of chlorine sanitizers such as aqueous sodium hypochlorite solution (bleach) or solid calcium hypochlorite to water generates a mixture of hypochlorous acid (HOCl) and hypochlorite ion (OCl$^-$) known as "free chlorine." The pool industry typically recommends that a free chlorine concentration of between 1.0 and 3.0 ppm be maintained in the swimming pool to provide for effective sanitation. Hypochlorous acid is a more effective disinfectant and oxidant than the hypochlorite ion, and their relative proportions fluctuate with the pH of the water in the pool (low pH is more acidic and high pH is more basic). At high pH, free chlorine will be mostly in the form of hypochlorite and so it will be less effective as a sanitizer. Thus, measuring free chlorine alone does not assure efficacy. Both the pH and free chlorine levels of swimming pool water must be monitored to ensure that an adequate water quality level is maintained.

Chlorine and bromine are both members of the same chemical family known as halogens. While not as popular as chlorine, bromine has gained wide acceptance as a sanitizer, especially in hot tubs where the hot turbulent water tends to increase the amount of wastes in the water. Bromine tablets, sticks or caplets are usually applied through some type of feeder device either in-line or, in some cases, as a floater-type feeder. The two-product system relies upon the addition of small amounts of an inert sodium bromide salt, which by itself does little. The water is then treated with an oxidizer especially suited for this purpose, or with chlorine. The oxidizer or chlorine acts to convert sodium bromide into "free bromine", a mixture of hypobromous acid (HOBr) and hypobromite ion (OBr$^-$). However, unlike chlorine, the amount of hypobromous acid present is less dependent on pH. Additionally, the bromamines formed when HOBr reacts with waste in the water do not cause eye and skin irritation or foul odors.

Alternatively, there is another way of testing the water called oxidation-reduction potential (ORP). ORP is a measure, in millivolts, of the tendency of a chemical substance to oxidize or reduce another chemical substance. A positive voltage indicates an oxidizing solution and a negative voltage indicates a reducing solution. ORP measurements are valid over a wide pH range, and provide an index of water quality based on activity of a sanitizer rather than just its quantity. The lower oxidation potential of bromine compared to chlorine means that ORP will not be as sensitive to the concentration of bromine as it will to chlorine. In 1988 the National Swimming Pool Institute adopted a standard of ORP value of greater than or equal to 650 mV for public spas. An ORP greater than or equal to 650 millivolts is adequate to kill viral and bacterial pathogens within seconds.

Another swimming pool water parameter that is important to determine is the amount of total dissolved solids (TDS). TDS is the sum of all materials dissolved in the water, and normally runs in the range of 250 ppm and higher. TDS can be salts like sodium chloride and calcium chloride, metals like iron, copper, and manganese, and dissolved organic compounds. The guideline for the maximum amount of total dissolved solids allowed in pool/spa water is <6000 ppm and in at least some environments <1500 ppm. At elevated levels, TDS can lead to cloudy or hazy water, difficulty in maintaining water balance, reduction in sanitizer activity, and foaming. It can also inhibit the sanitizer efficiency to the point that algae plumes form even though tests indicate an acceptable free chlorine level. When this problem is identified, the only way to reduce TDS is to drain a portion of the water and replace it with fresh water.

It is desirable to have sensors that can monitor water quality parameters automatically and frequently, even continuously. Sensors for such measurements often operate on a potentiometric electrochemical principle that incorporates a reference electrode and a sensing electrode. Conventional reference electrodes for use in such potentiometric electrochemical measurements typically incorporate an internal reference fill solution in contact with an electrode in contact with a test solution through a porous junction, which allows a slow leak of the internal reference fill solution to provide the necessary electrolytic contact with the liquid being tested. A metal or electrochemical electrode in contact with the test solution completes the circuit and an electrical potential on the reference electrode remains relatively constant while the sensing electrode responds to chemical changes in the test solution.

Conventional sensors of this type suffer from several drawbacks when applied to certain measurement environments. One problem is that chemicals employed to sanitize the water can interfere with the measurements. Conventional electrodes of this type suffer from several drawbacks when applied to certain measurement environments, such as long-term unattended monitoring of pool or spa water. For example, because leakage of the internal reference fill solution through the porous junction into the tested environment is necessary to provide electrolytic conductivity between the internal reference fill solution and the tested environment, the useful life of the reference electrode is limited. Moreover, a high rate of leakage is desirable to produce a low electrical impedance of the reference electrode. Moreover, in a pipe mounted system, the flow of test solution flowing over the electrode exacerbates the high leakage rate. Thus, while low electrical impedance is desirable for accurate measurements because it reduces noise, the high leakage rate employed in such conventional reference electrodes to produce the desired low electrical impedance severely limits the life of the electrode and the electrode must be frequently refilled with fresh internal solution or replaced.

Such conventional reference electrodes suffer from other disadvantages as well. For example, they tend to be fragile, typically being encased in glass. Moreover, they often are limited in operational orientation. In other words, because the reference fill solution of the electrode is a liquid, it readily flows as a result of gravity. Thus, the relative orientation of the electrode with respect to the reference fill solution and the reference fill solution with respect to the porous junction depends on the spatial orientation of the electrode and so the electrode assembly in the test solution must be oriented vertically so that the reference fill solution is properly oriented in the electrode. Indeed, silver/silver chloride reference electrodes suspended in glass-encased fill solutions have been employed in combination with antimony electrodes in some pH sensors, with all the attendant disadvantages of glass membranes and fill solutions noted above.

U.S. Pat. No. 8,574,413, the entire contents of which are hereby incorporated by reference, discloses electrochemical sensors for measuring certain characteristics of aqueous liquids.

What is needed are sensors that are precise and reliable and can accurately monitor various water quality parameters such as pH, free chlorine level, ORP, and TDS over an extended period of time. In particular, it would be desirable to have sensors that are individually calibrated and have their own memory device. Further, it would be desirable to interface such sensors with control equipment so that appropriate water quality adjustments can be made to ensure the water is healthful. The plurality of sensors of the present invention is robust and provide for long periods of unattended operation.

SUMMARY

In one form, a sensing device comprises a sensor configured to sense a first parameter and a second parameter of a liquid and having an analog output port configured to provide a first analog signal indicative of the sensed first parameter and configured to provide a second analog signal indicative of the sensed second parameter. The sensor has a calibration memory device storing individual digital information indicative of a calibration of the first parameter relative to the second parameter and has a digital output port providing a digital signal indicative of the digital information.

In another form, a treatment system and/or method employ the sensor.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

The present invention comprises sensors, each of which is individually calibrated and has its own memory device storing individualized calibration information. For example, such sensors comprise chlorine sensors, total dissolved solids (TDS) sensors, oxygen reduction potential (ORP) sensors, and/or pH sensors. The present invention also comprises systems and methods which use such sensors. The various sensors of the present invention may be employed in system combinations in any desired permutation. For example, a pH sensor may be used alone or in combination with a chlorine sensor, an ORP sensor, and/or a TDS sensor.

Other sensors, such as a temperature sensor, can be employed in any of such combinations.

Figure 1:
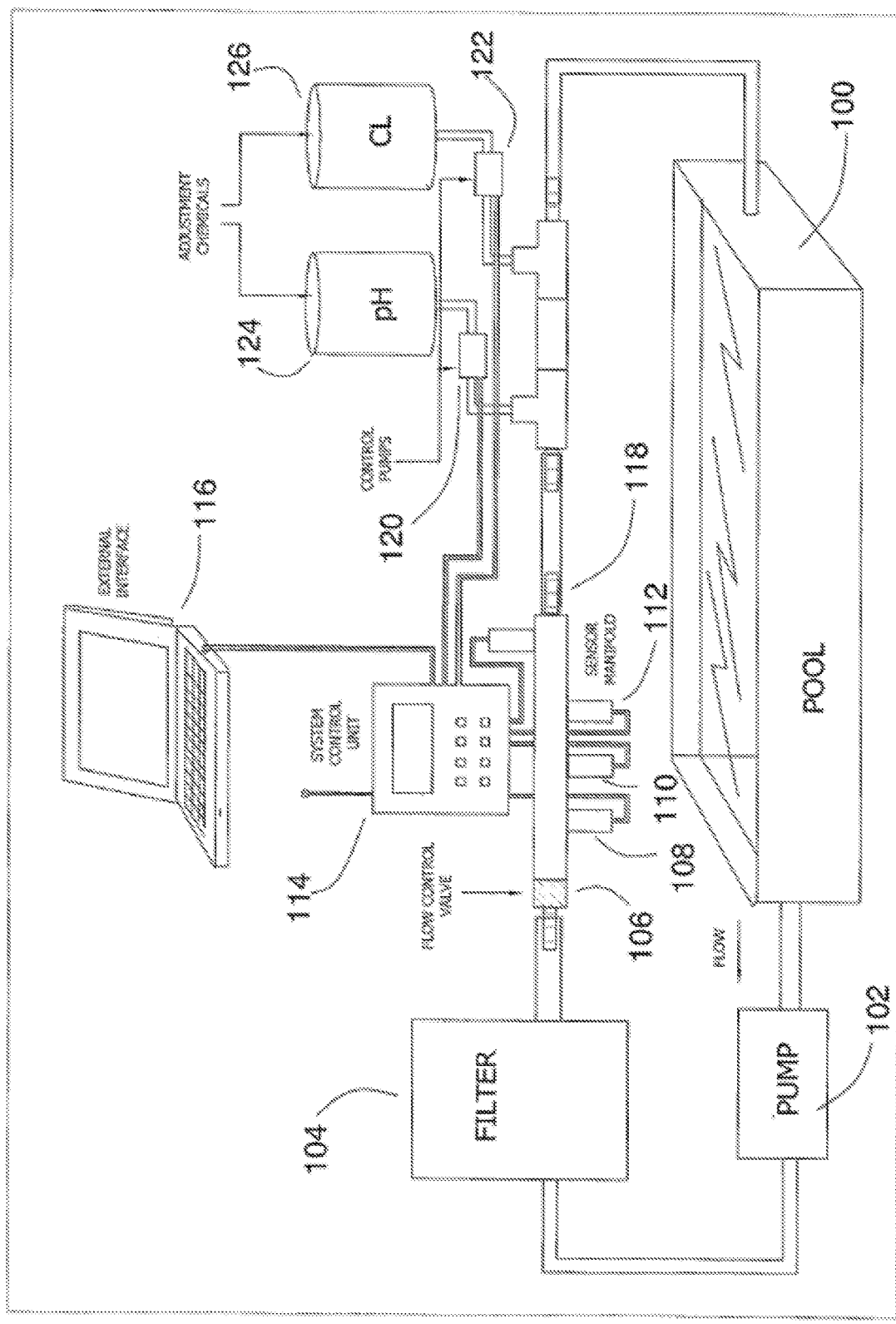
FIG. 1 is a diagram of a system according to one embodiment of the invention illustrating, schematically, a measurement system combining three sensors of the present invention in a pool treatment situation.
Figure 2:
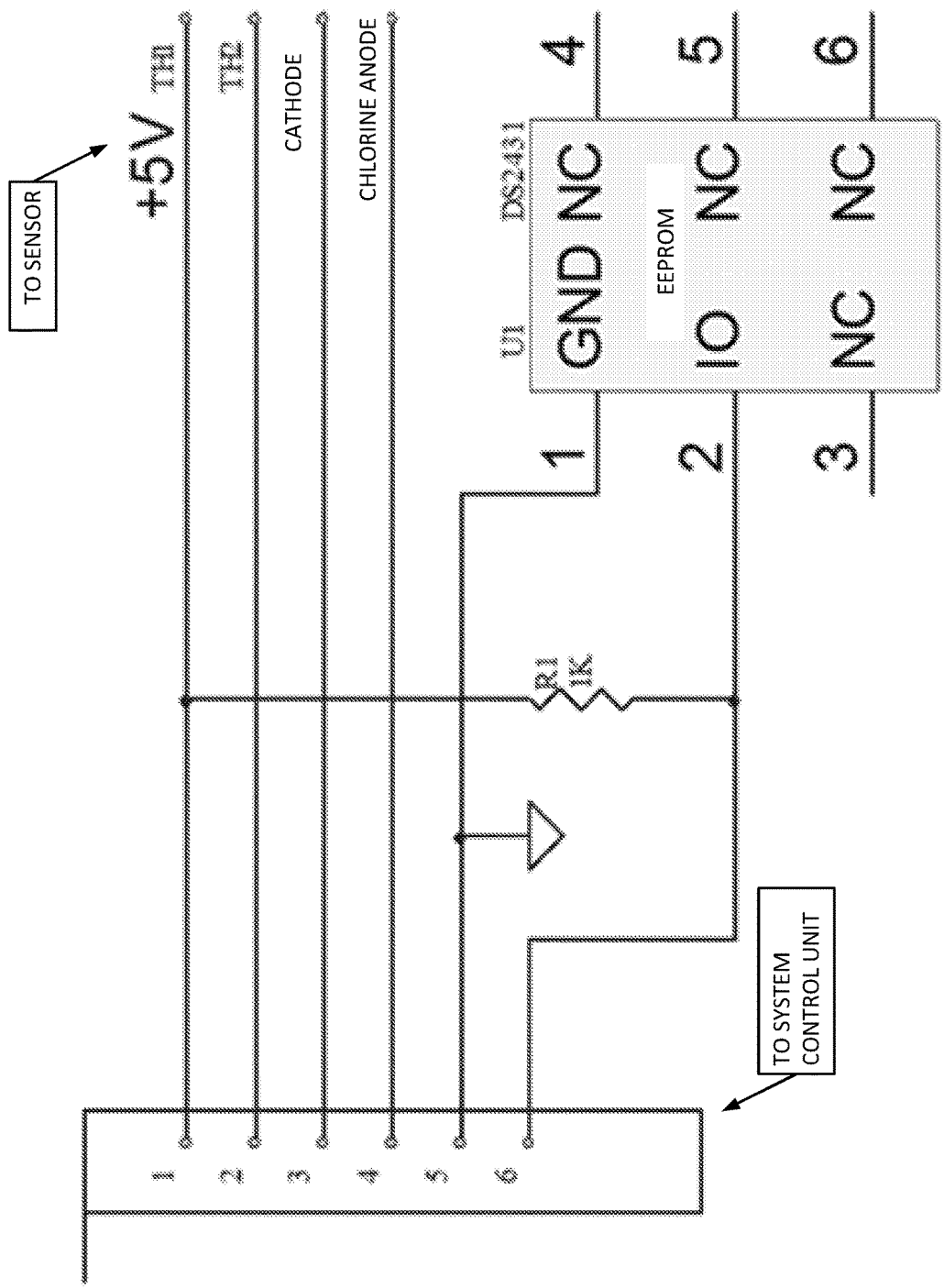
FIG. 2 is a schematic diagram of a chlorine sensor circuit.

FIG. 1 illustrates, schematically, a measurement system combining three sensors of the present invention in a pool treatment situation. As can be seen from FIG. 1, water from a pool 100 is pumped via pump 102 through a filter 104 and then a flow sensor 106, to a chlorine sensor (i.e. measures free chlorine level, FCL) 108, a pH sensor 110, and an ORP sensor 112 of the present invention. The output from the sensors 106, 108, 110, and 112 are sent to a system control unit 114, also controlled by an external interface 116 (such as a mobile device or computer having a display), which can enter adjustments and desired settings, such as desired pH or chlorine content of the pool water, into the system control unit 114. The flow sensor 106 is used to compensate the signal on the chlorine sensor since the output of the chlorine sensor is proportional to the flowrate. This compensation is an important feature when using variable speed pumps. The system control unit 114 controls a sensor manifold 118 and control pumps (or valves) 120 and 122, which, according to instructions from system control unit 114 (and external interface 116), meter pH-adjusting chemicals and chlorine from supply tanks 124 and 126, respectively, into the water pumped from the pool, after which the water is recycled back into pool 100.

In one embodiment of the sensor there is a memory circuit (such as an EEPROM) placed inside the sensor housing. The memory circuit is used to store calibration and other information such as device identification (ID) and/or a serial number. The central benefit of this configuration is that it provides a high level of traceability to the measurement system. It also allows for storing other user defined data.

Figure 6:
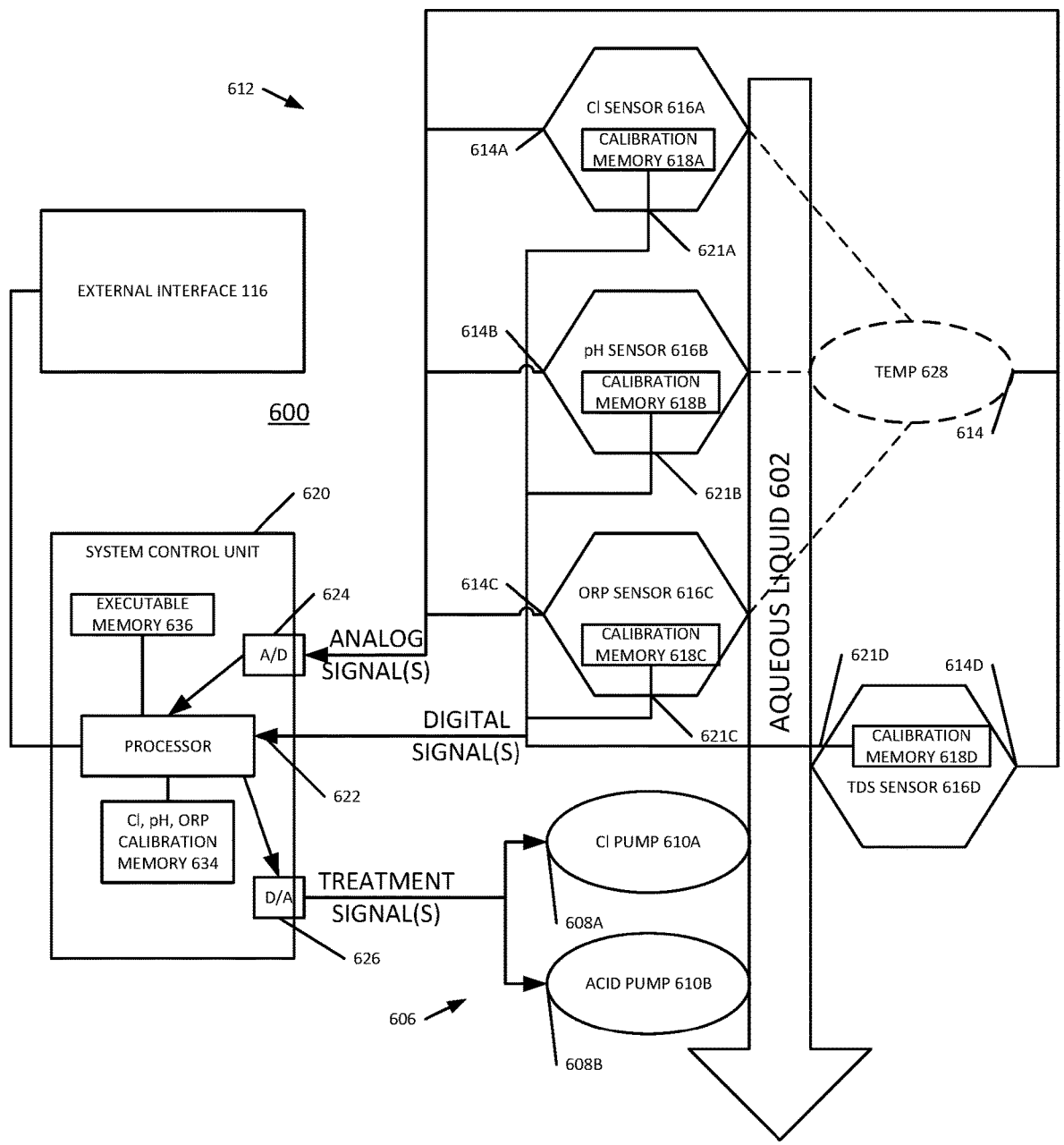
FIG. 6 is a block diagram of sensors and a system control unit according to an embodiment of the invention.
Figure 7:
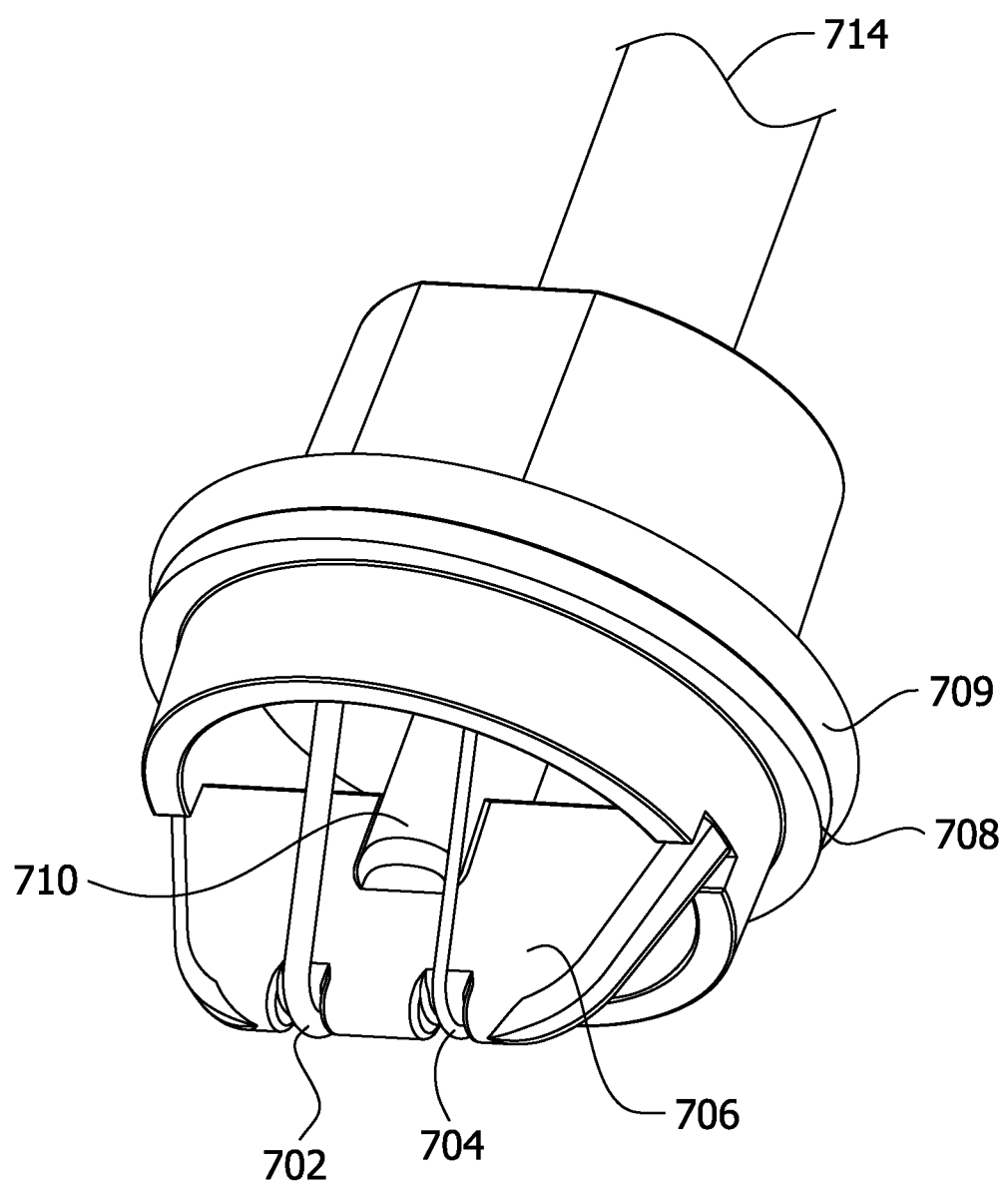
FIG. 7 is a perspective view of a sensor according to one embodiment of the invention.
Figure 8:
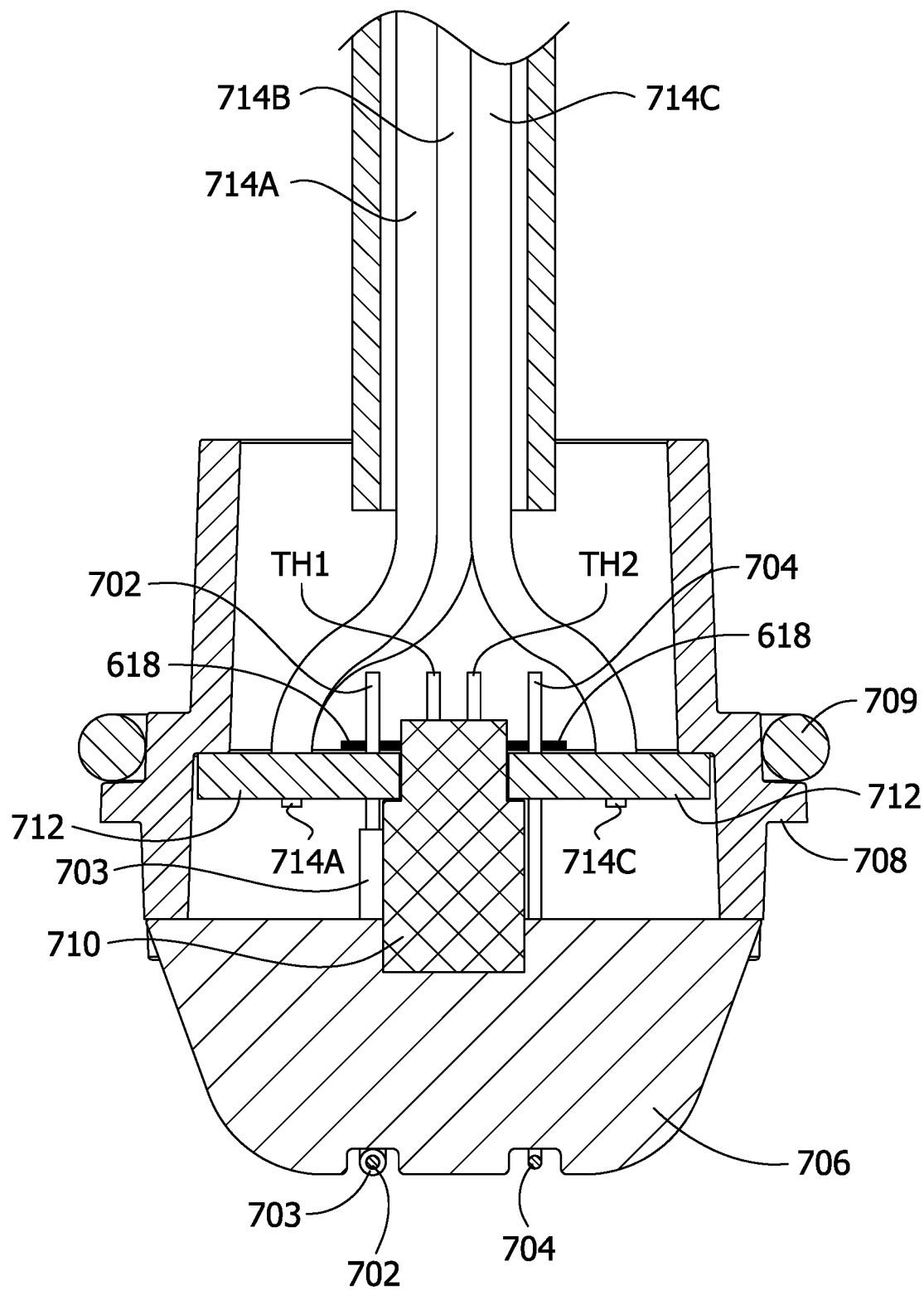
FIG. 8 is cross-sectional view taken along lines 8-8 of FIG. 9.
Figure 9:
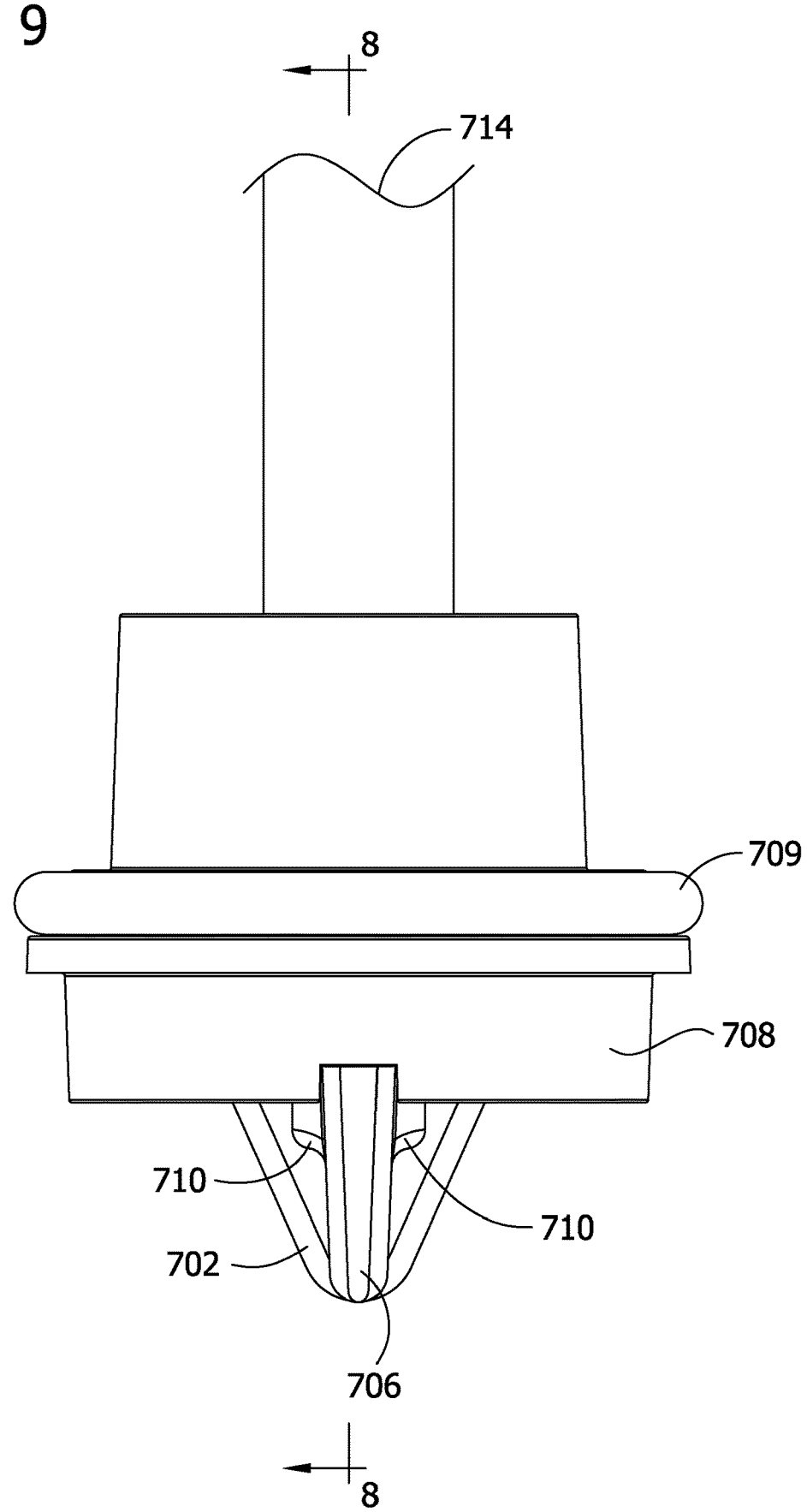
FIG. 9 is right side view of the sensor of FIG. 7.

FIG. 6 is a block diagram of sensors and a system control unit according to an embodiment of the invention. In one form, FIG. 6 illustrates a treatment system 600 for treating a liquid such as an aqueous liquid 602. A conduit 604 channels the aqueous liquid 602 to be treated. A treatment device 606 associated with the conduit alters the aqueous liquid 602 and has an input port 608 for receiving a treatment signal indicative of an extent to which the treatment device 606 alters the aqueous liquid 602. For example, the treatment device 606 can be a chlorine pump 610A having a control input port 608A and/or an acid pump 610B having a control input port 608B. One or more sensors 612 sense a parameter of the aqueous liquid 602 and have an analog output port 614 providing analog signals indicative of the sensed parameters. For example, the sensor 612 can be a chlorine sensor 616A, a pH sensor 616B, an ORP sensor 616C, and/or a TDS sensor 616D located within the conduit 604 (e.g., within a manifold). Each sensor has a calibration memory device 618 (e.g., an EEPROM or a tangible, non-transitory storage memory) storing digital information indicative of a calibration of the sensor 616 and has a digital output port 621 providing a digital signal indicative of the digital information. In addition, each sensor 612 senses a second parameter of the aqueous liquid 602 and provides a second analog signal via analog output port 614 indicative of second sensed parameter. For example, the second parameter comprises temperature of the aqueous liquid 602 in which case the calibration memory device 618 (e.g., an EEPROM) stores digital information indicative of a temperature-compensated calibration of the sensor 616 and has a digital output port 621 providing a digital signal indicative of the digital information. In one embodiment, the calibration memory device 618 is an integral part of the sensor 612 so that the calibration memory device 618 is embedded within the sensor 612 and enclosed by the sensor 612, such as illustrated in FIGS. 7-9. Thus, the calibration memory device 618 and the sensor 612 comprise a unitary component within a housing.

A system control unit, i.e., controller 620, has a digital input port 622 connected to the digital output port 621 of the sensor 616. The controller 620 receives the digital signal via its digital input port 622 and determines a calibration of the sensor 612. The controller 620 has an analog input port (e.g. an analog-to-digital (A/D) converter 624) connected to the analog output port 614 of the sensor 612. The controller 620 receives the analog signal via its analog input port and determines the parameter of the aqueous liquid based on the received analog signal and based on the received digital signal. The controller has an output port connected to the treatment device 606 providing the treatment signal to the input port of the treatment device. The treatment signal is configured to control the treatment device 606 as a function of the determined parameter by controlling the extent to which the treatment device alters the aqueous liquid 602.

The treatment device 606 in one form comprises a chlorine supplier such as chlorine pump 610A or a chlorine generator for adding free chlorine to the aqueous liquid 602. The treatment signal is indicative of an amount of free chlorine added to the aqueous liquid or is indicative of a rate at which free chlorine is added to the aqueous liquid. The sensor comprises a chlorine sensor 616A sensing a free chlorine level of the aqueous liquid 602 and the analog signal is indicative of the free chlorine level of the aqueous liquid. The controller 620 determines the free chlorine level of the aqueous liquid 602 based on the received analog signal and based on the received digital signal. The treatment signal provided by the output port (e.g., a digital-to-analog (D/A) converter 626) of the controller is configured to control the chlorine supplier as a function of the determined free chlorine level of the aqueous liquid 602 as compared to a minimum free chlorine level by controlling the amount of free chlorine added to the aqueous liquid 602 by the chlorine supplier or the rate at which free chlorine is added to the aqueous liquid 602 by the chlorine supplier.

In one form, the treatment device 606 comprises an acid supplier such as acid pump 610B for adding acid to the aqueous liquid. The treatment signal is indicative of an amount of acid added to the aqueous liquid or is indicative of a rate at which acid is added to the aqueous liquid. The sensor 612 comprises a pH sensor 616B sensing a pH level of the aqueous liquid and wherein the analog signal is indicative of the pH level of the aqueous liquid. The controller 620 determines the pH level of the aqueous liquid based on the received analog signal and based on the received digital signal. The treatment signal provided by the output port of the controller is configured to control the acid supplier as a function of the determined pH level of the aqueous liquid as compared to a maximum pH level by controlling the amount of acid added to the aqueous liquid by the acid supplier or the rate at which acid is added to the aqueous liquid by the acid supplier.

In one form, the treatment device 606 comprises a chlorine supplier such as chlorine pump 610A for adding free chlorine to the aqueous liquid 602. The treatment signal is indicative of an amount of free chlorine added to the aqueous liquid 602 or is indicative of a rate at which free chlorine is added to the aqueous liquid 602. The sensor 612 comprises an ORP sensor 616 sensing a free chlorine level of the aqueous liquid 602. The analog signal is indicative of the free chlorine level of the aqueous liquid.

The controller 620 determines the free chlorine level of the aqueous liquid 602 based on the received analog signal and based on the received digital signal. The treatment signal provided by the output port 626 of the controller is configured to control the chlorine supplier as a function of the determined free chlorine level of the aqueous liquid 602 as compared to a minimum free chlorine level by controlling the amount of chlorine added to the aqueous liquid by the chlorine supplier or the rate at which free chlorine is added to the aqueous liquid by the acid supplier.

Each of the above sensors 612 includes a temperature sensing device 628 sensing a temperature of the aqueous liquid 602. For ease of illustration, the temperature sensing device 628 is illustrated separately in phantom in FIG. 6. It is understood that each of the chlorine sensor 616A, the pH sensor 616B, the ORP sensor 616C, and optionally the TDS sensor 616D each have a temperature sensing device such as a thermistor, as illustrated in FIGS. 7-9. The analog output port 614 provides a temperature signal indicative of the sensed temperature, although it is contemplated that the temperature sensing device can provide a digital signal via digital output port 621. For analog temperature sensing devices, the controller 620 receives the temperature signal via A/D converter 624. For digital temperature sensing devices, the controller 620 receives the temperature signal via digital input port 622. The controller 620 determines the temperature of the aqueous liquid 602 based on the temperature signal, and provides the treatment signal as a function of the determined temperature.

Figure 3:
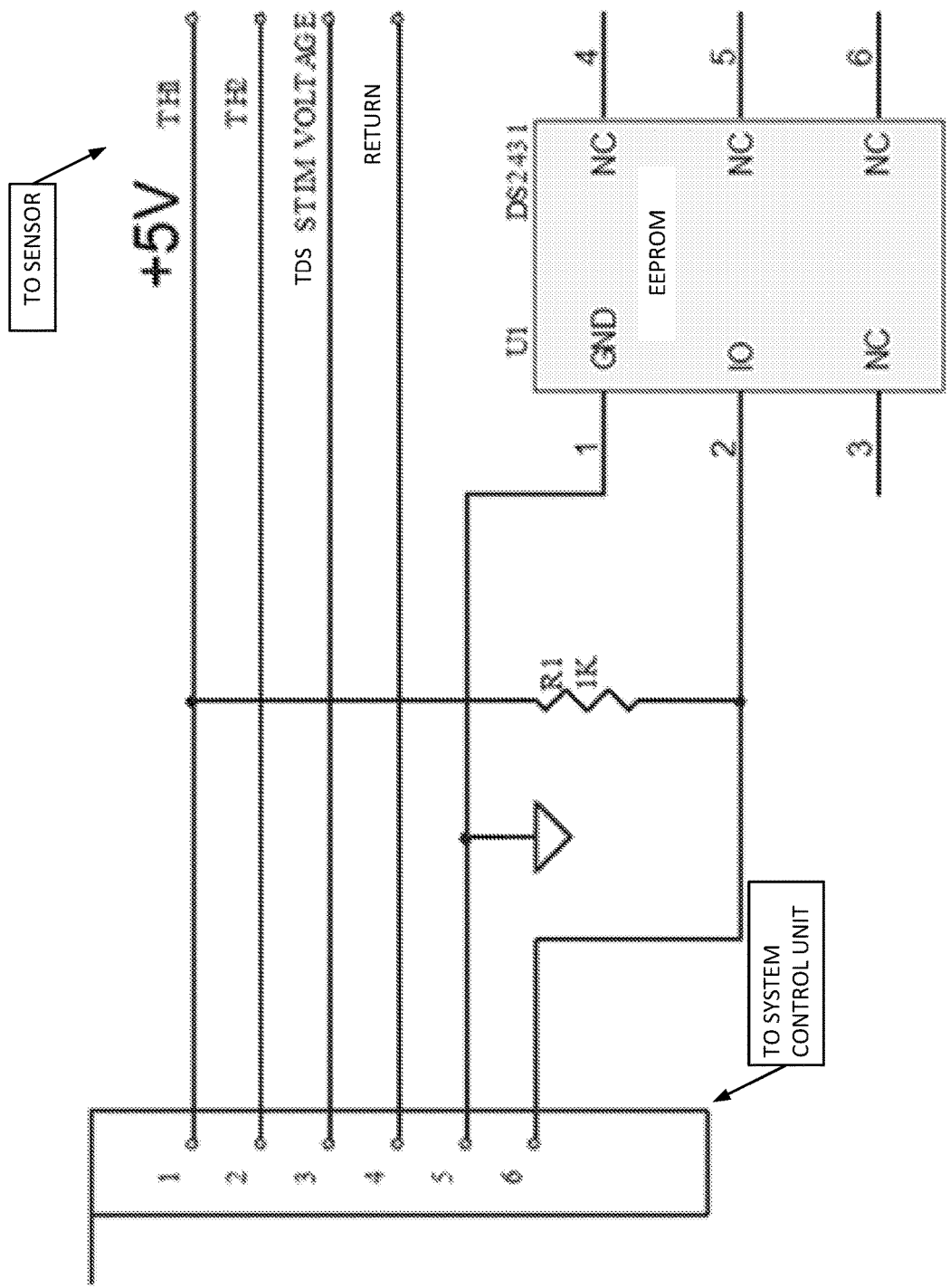
FIG. 3 is a schematic diagram of a TDS sensor circuit.
Figure 4:
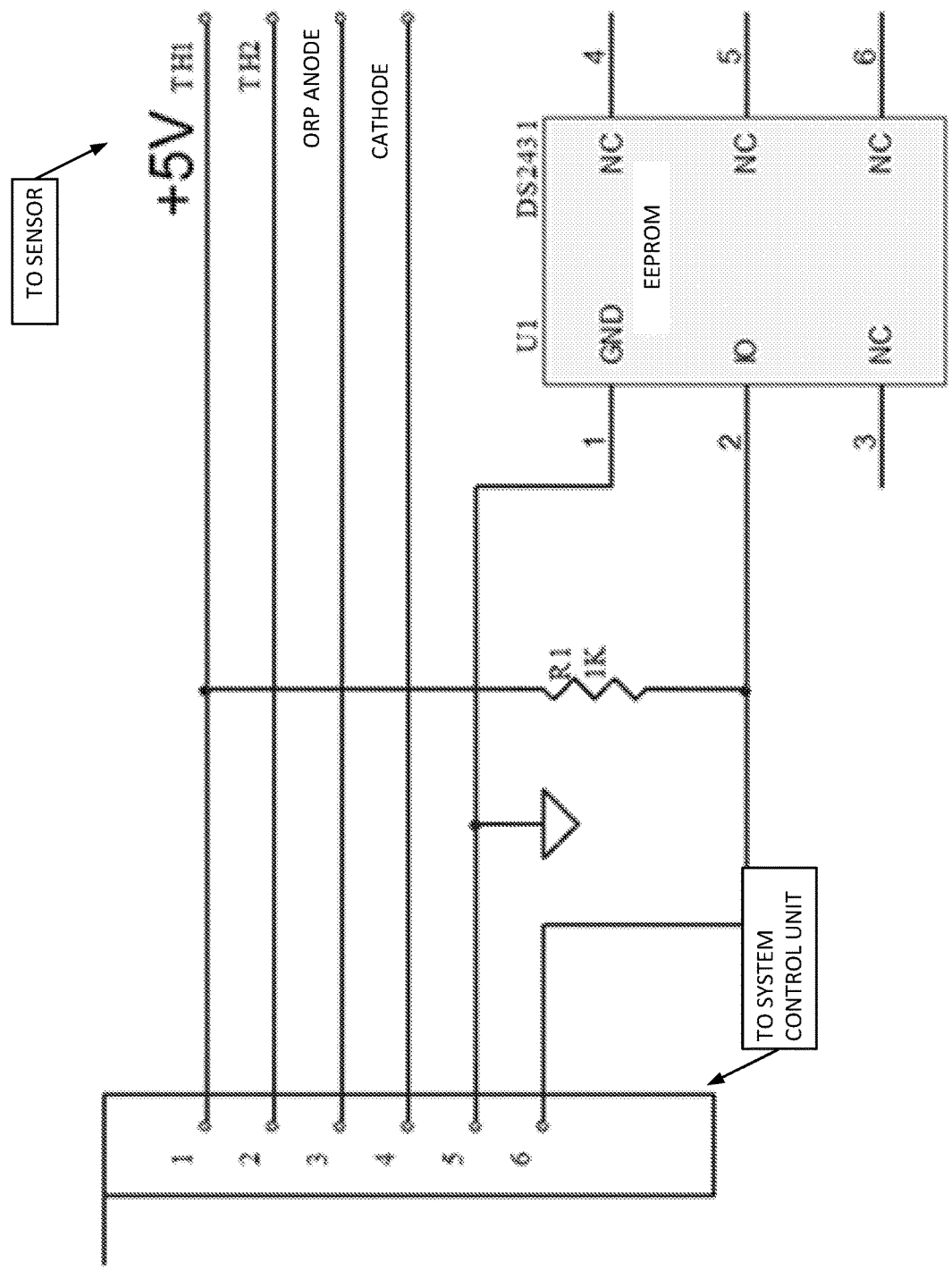
FIG. 4 is a schematic diagram of an ORP sensor circuit.

In one form, the sensor comprises a TDS sensor (see FIG. 3) sensing a TDS ppm salt level of the aqueous liquid 602. The analog signal 614 is indicative of the TDS ppm salt level of the aqueous liquid 602. The controller 602 determining the TDS ppm salt level of the aqueous liquid 602 based on the received analog signal and based on the received digital signal, the controller 602 provides an indication such as a notice on the external interface 116 and/or an alarm when the determined TDS ppm salt level of the aqueous liquid 602 is greater than a maximum.

As shown in FIGS. 2-5, the calibration memory device comprises an EEPROM (e.g., DS2341) storing some or all of the following temperature compensation information (see Table 2 below): a high or low gain, an offset, and an analog-to-digital conversion value of the analog signal indicative of the sensed parameter. In FIGS. 2-5, the solder pads are numbered the same as the connector for clarity. Terminals 1 and 2 of the EEPROM DS2341 are connected to terminals 5 and 6 of the connector which is connected to the controller 620 providing and/or receiving the stored digital information. Terminal 1 is a ground port and terminal 2 is an input/output (I/O) port.

The other terminals of the EEPROM DS2341 are not used. In general, each sensor 612 measures two parameters of a liquid such as an aqueous liquid and the calibration memory device stores information to calibrate one parameter relative to the other parameter.

Alternatively or in addition, the EEPROM stores the following information: two or more temperature coefficients for adjusting the analog signal indicative of the sensed parameter, and/or the controller 620 includes a controller calibration memory device 634 in which the controller 620 reads the sensor calibration memory device 618 and stores the digital information stored in the calibration memory device 634 of the sensor 612. As a default, the controller can be configured to calibrate the sensor 612 in the event that the digital information stored in the calibration memory device 618 of the sensor is not valid, or the controller is configured with a memory device (not shown) having default calibration information in the event that the digital information stored in the calibration memory device 618 of the sensor 612 is not valid. Optionally, the digital information stored in the calibration memory device 618 of the sensor 612 is encrypted and the controller 620 is configured to decrypt the encrypted digital information.

Optionally, the controller 620 stores a plurality of identification information identifying selected sensors 612. The controller 620 is configured to disable an operation of the system 600 if the calibration memory device 618 of the sensor 612 having its digital output port 614 connected to the digital input port 622 of the controller 620 does not have identification information which corresponds to (e.g. matches) the identification information stored in the controller memory device 634. As a result, only selected sensors 612 will operate with selected systems 600 to prevent a mismatch between a sensor 612 and the system 600 to which it is connected.

In one form, controller 620 is a microcontroller which communication to the memory 618 on each sensor 612 using a simple two wire connection on the sensor connector. (See the schematics illustrated in FIGS. 2-5) A standard method based on the "1-Wire Protocol" such as implemented using a MAXIM DS2431 or similar circuitry can be used as the method of communication. The microprocessor detects when a sensor 612 is connected and retrieves the information from its EEPROM 618. Executable software stored in memory 636 prompts for overwrite then processes the input data and displays it on an LCD or other display device (such as a display of the external interface 116, not shown). Each circuit also has a communication port available to connect to an external interface 116 to read/write the EEPROM data for manual editing. The EEPROM data can be encrypted to prevent viewing/editing without authorization.

In one form, the communication is through a "one wire" interface (such as IEEE P1451.4 Smart Sensor Interface) provided by a Dallas Semiconductor Corp DS2431 1-wire EEPROM. The interface uses a pull-up resistor from the I/O line of a microcontroller to both power the device and communicate with it. (See APPLICATION NOTE 2966 MINIMAL REMOTE 1-WIRE® MASTER Protocol from Maxim Integrated Circuits and DS2431 Datasheet.)

Each sensor 612 can be assigned its own unalterable and unique 64-bit ROM registration number that is factory lasered into the chip. This gives every sensor 612 a unique identification number. In this case each sensor will have a unique "serial number".

The following Table 1 illustrates the various parameters detected by the sensors 612.

TABLE 1

Figure 5:
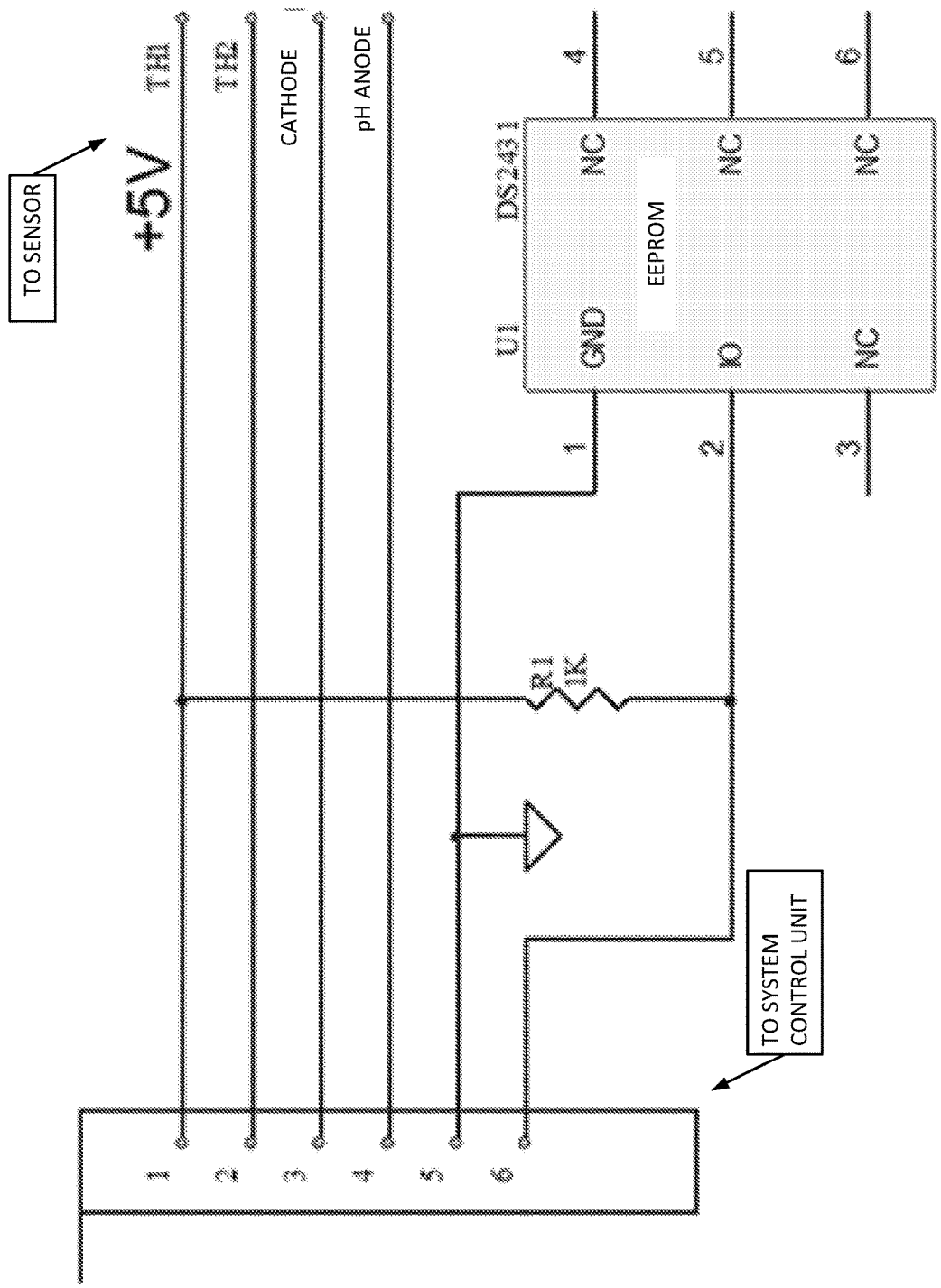
FIG. 5 is a schematic diagram of a pH sensor circuit.

| Sensor | Analyte | Desired Level | Chemical Treatment | Example(s) |
| --- | --- | --- | --- | --- |
| pH FIG. 5 | Hydrogen ions | A current signal indicative of a pH | Muriatic acid, a solution of hydrogen chloride in water, is added | The Hayward AQL-CHEM-2-240 is a $CO_2$ dispensing system. To lower pH, a manifold |

TABLE 1-continued

| Sensor | Analyte | Desired Level | Chemical Treatment | Example(s) |
|---|---|---|---|---|
| | | of 7.2 to 7.8 | to lower pH. The acid feed system is a 4:1 dilution of 20 degree Baume hydrochloric acid (31.45 wt. %) in water. The Baume scale measures the density of liquids heavier than water. The Baume of distilled water is 0. Hydrochloric acid is available in concentrations ranging from 4 to 23 degree Baume. | connects to a carbon dioxide tank. $CO_2$ reduces pH by forming carbonic acid ($H_2CO_3$). Alternatively, the Sense and Dispense system supports the Stenner Pump acid feed system. AQL-CHEM-3-120 is an automatic acid dispensing system to lower the pH level of pool water. It utilizes a Stenner S1G45MJL3F2S/W2S series acid pump and 15 gallon tank. |
| ORP FIG. 4 | "Free chlorine"- a combination of hypochlorous acid (HOCl) and hypochlorite ion ($OCl^-$) providing a millivolt level primarily indicative of an oxidizing power of the water | A voltage signal ≥650 mV | Generate "free chlorine" from NaCl. | AQL-CHEM is a pH and ORP sensing kit which uses a chlorine generator to increase the level of free chlorine. A chlorine generator (also known as a salt cell, salt generator, or salt chlorinator) uses electrolysis in the presence of dissolved salt (NaCl) to produce hypochlorous acid (HOCl) and sodium hypochlorite (NaOCl). |
| Chlorine FIG. 2 | "Free chlorine"- a combination of hypochlorous acid (HOCl) and hypochlorite ion ($OCl^-$). | A current signal indicative of 1.0 to 3.0 ppm. | Generate "free chlorine" from NaCl. | Same as ORP. |
| TDS FIG. 3 | A salt level indicative of Total Dissolved Solids - all conductive materials dissolved in the water. Responsive to salts like sodium chloride and calcium chloride, minerals like copper, iron, and manganese, and electro-active ionic materials. | A current signal indicative of <6000 ppm or A current signal indicative of <1500 ppm. | None. To reduce TDS, a portion of the water must be drained and replaced with fresh water. | Hayward Sense and Dispense Chemistry Automation |

Typical Sequence of Operation

New Sensor Connection

If no sensor is connected, the controller 620 continually issues a reset signal (I/O Line low for 480 μs) and waits for the Presence signal consisting of the Slave pulling the line low within 60 μs from the time the controller 620 releases the line. When the controller 620 senses the presence of a sensor 612, it goes through an ID process that reads the sensor file in memory 618 and makes sure that the correct sensor is attached. The controller 620 then copies the calibration and ID information into its' own internal memory 634. It then prompts to overwrite the current calibration file.

In one form, the software in memory 636 can notify a user if the sensor is different from the one it remembers. If there is not a valid calibration file in the sensor, the operator can be given two choices. Calibrate or Use raw ADC (default) values. If Calibration is chosen, the instrument will go into CALIBRATION MODE in which the sensor is recalibrated.

Calibration Procedure Sequence

Table 2 below indicates one embodiment for a table layout of calibration parameters and the number of bytes allocated for each for memory 618.

TABLE 2

| | Description | Type | Size (Bytes) |
|---|---|---|---|
| High | Gain | float | 4 |
| | Offset | float | 4 |
| | ADC | word | 2 |
| | Temperature*10 | word | 2 |
| Low | Gain | float | 4 |
| | Offset | float | 4 |
| | ADC | word | 2 |
| | Temperature*10 | word | 2 |
| Temp Comp | coeff a | float | 4 |
| | coeff b | float | 4 |
| | coeff c | float | 4 |

TABLE 2-continued

| Description | Type | Size (Bytes) |
|---|---|---|
| Date Month | byte | 1 |
| Day | byte | 1 |
| Year-2000 | byte | 1 |
| ID Sensor Type | byte | 1 |
| Version | word | 2 |
| Status | byte | 1 |
| Checksum | byte | 1 |
| Used | | 44 |
| Available | bytes | 128 |
| Free | | 84 |

In one form, some or all of the information in memory 618 can be encrypted to prevent reverse engineering. The calibration information in the memory 618 is used to convert the ADC values from the sensor along with the current temperature to calculate the desired temperature-compensated output variable (e.g., Free Chlorine, TDS, pH, ORP).

The calibration record of each sensor includes the signal level (in the units of the type of sensor) and the temperature at which it was measured at a high level of concentration and at a low level of concentration. Chlorine sensors are calibrated at a constant pH between 7.2 and 7.6.

As one example, chlorine sensor 616A may be calibrated as follows. The sensor 616A is tested at a first known temperature and at a first known FCL level and the millivolt level at its analog output port 614A indicative of the chlorine level is read and saved. The thermistor 710 of the chlorine sensor 616A can be used to determine the first temperature. As a specific example of this first reading, a sensor 616A at temperature 26.8° C. and at an FCL level of 0.40 ppm provides a first 262.51 mV output. The sensor 616A is again tested at a second known temperature (which may be different from the first temperature) and at a second known FCL level (different from the first FCL level) and the millivolt level at its output 614A is read and saved. As a specific example of this second reading, the same sensor 616A at temperature 26.2° C. and at an FCL level of 3.40 ppm provides a second 481.07 mV output. The temperature readings can be determined by reading the thermistor 628 of the sensor 616A. The first and second readings are stored in the calibration memory 618A. The first known temperature, the first known FCL, and the resulting first mV output reading are entered into a table, as shown in Table 3 below. The second known temperature, the second known FCL, and the resulting second mV output reading are entered into the same table. Additional readings are extrapolated from the first and second readings and added to the table to provide a calibration table with automatic temperature compensation. This calibration table is used by the system control unit 620 to scale the mV readings and then derive the chlorine concentration from the chlorine sensor 616A. Alternatively or in addition, the first and second readings are used to define an algorithm which is then used to interpret readings from the chlorine sensor 616A. The table and/or algorithm can be stored in the calibration memory 618A and/or can be part of the system control unit 620.

TABLE 3

| Temp 1 | 26.8° C. | FCL 1 | 0.40 ppm | mV 1 | 262.51 |
| Temp 2 | 26.2° C. | FCL 2 | 3.40 ppm | mV 2 | 481.07 |

By recalling both the first and second known temperature values, the first and second known FCL values, and the first and second known mV readings, the system control unit 620 derives a linear formula of chlorine values in the form of Y=mX+b, wherein Y can be defined as FCL level or temperature compensated mV reading and X is defined as the opposite value. Both m and b values are then stored into memory on sensor 616A and recalled by the system control unit 620 to calculate FCL reading from the current mV value output by sensor 616A, if needed. As an example, if Y is defined as FCL level, then X is defined as temperature compensated mV reading. To define m, the system control unit 620 will divide the difference between the second known FCL level (3.40) and the first known FCL level (0.40) by the difference between the second known mV level (481.07) and the first known mV level (262.51). The system control unit 620 will use substitution to define b for the above formula by using the second known FCL level (3.40) as X, the second known mV level (481.07) as Y, and m as defined above.

As another example, pH sensor 616B may be calibrated as follows. The sensor 616B is tested at a first known temperature and at a first known pH level and the millivolt level at its analog output port 614B indicative of the pH level is read and saved. The thermistor 710 of the pH sensor 616B can be used to determine the first temperature. As a specific example of this first reading, a sensor 616B at temperature 26.8° C. and at a pH level of 6.91 provides a first 2158.73 mV output. The sensor 616B is again tested at a second known temperature (which may be different from the first temperature) and at a second known pH level (different from the first pH level) and the millivolt level at its output 614B is read and saved. As a specific example of this second reading, the same sensor 616B at temperature 26.2° C. and at a pH level of 7.77 provides a second 2424.91 mV output. The temperature readings can be determined by reading the thermistor 628 of the sensor 616B. The first and second readings are stored in the calibration memory 618B. The first known temperature, the first known pH, and the resulting first mV output reading are entered into a table, as shown in Table 4 below. The second known temperature, the second known pH, and the resulting second mV output reading are entered into the same table. Additional readings are extrapolated from the first and second readings and added to the table to provide a calibration table with automatic temperature compensation. The calibration table is used by the system control unit 620 to scale the mV readings and then derive the pH level from the pH sensor 616B. Alternatively or in addition, the first and second readings are used to define an algorithm which is then used to interpret readings from the pH sensor 616B. The table and/or algorithm can be stored in the calibration memory 618B and/or can be part of the system control unit 620.

TABLE 4

| Temp 1 | 26.8° C. | pH | 6.91 | mV 1 | 2158.73 |
| Temp 2 | 26.2° C. | pH | 7.77 | mV 2 | 2424.91 |

By recalling both the first and second known temperature values, the first and second known pH values, and the first and second known mV readings, the system control unit 620 derives a linear formula of pH values in the form of Y=mX+b, wherein Y can be defined as pH level or temperature compensated mV reading and X is defined as the opposite value. Both m and b values are then stored into memory on sensor 616B and recalled by the system control unit 620 to calculate pH reading from the current mV value output by sensor 616B, if needed. As an example, if Y is defined as pH level, then X is defined as temperature compensated mV reading. To define m, the system control unit 620 will divide the difference between the second known pH level (7.77) and the first known pH level (6.91) by the difference between the second known mV level (2424.91) and the first known mV level (2158.73). The system control unit 620 will use substitution to define b for the above formula by using the second known pH level (7.77) as X, the second known mV level (2424.91) as Y, and m as defined above.

As another example, ORP sensor 616C may be calibrated as follows. For ORP, a reference chlorine measurement is made and stored relative to a specific mV output from sensor 616C. Measurements are repeated at regular intervals (6 months or 1 time/season) to gauge sensor drift. There is no computational derivative of the values stored in sensor 616C.

As another example, TDS sensor 616D may be calibrated as follows. The sensor 616D is tested at a first known temperature and at a first known pH level and the millivolt level at its analog output port 614D indicative of the TDS level is read and saved. The thermistor 710 of the TDS sensor 616D can be used to determine the first temperature. As a specific example of this first reading, a sensor 616D at temperature 26.8° C. and at a TDS level of 918 ppm provides a first 545.79 mV output. The sensor 616D is again tested at a second known temperature (which may be different from the first temperature) and at a second known TDS level (different from the first TDS level) and the millivolt level at its output 614D is read and saved. As a specific example of this second reading, the same sensor 616D at temperature 26.2° C. and at a TDS level of 3430 ppm provides a second 1960.93 mV output. The temperature readings can be determined by reading the thermistor 628 of the sensor 616D. The first and second readings are stored in the calibration memory 618D. The first known temperature, the first known TDS, and the resulting first mV output reading are entered into a table, as shown in Table 5 below. The second known temperature, the second known TDS, and the resulting second mV output reading are entered into the same table. Additional readings are extrapolated from the first and second readings and added to the table to provide a calibration table with automatic temperature compensation is used by the system control unit 620 to scale the mV readings and then derive the TDS level from the TDS sensor 616D. Alternatively or in addition, the first and second readings are used to define an algorithm which is then used to interpret readings from the TDS sensor 616D. The table and/or algorithm can be stored in the calibration memory 618D and/or can be part of the system control unit 620.

TABLE 5

| Temp 1 | 26.8° C. | TDS | 918 ppm | mV 1 | 545.79 |
| Temp 2 | 26.2° C. | TDS | 3430 ppm | mV 2 | 1960.93 |

By recalling both the first and second known temperature values, the first and second known TDS values, and the first and second known mV readings, the system control unit 620 derives a linear formula of TDS values in the form of Y=mX+b wherein Y can be defined as TDS level or temperature compensated mV reading and X is defined as the opposite value. Both m and b values are then stored into memory on sensor 616D and recalled by the system control unit 620 to calculate pH reading from the current mV value output by sensor 616D, if needed. As an example, if Y is defined as TDS level, then X is defined as temperature compensated mV reading. To define m, the system control unit 620 will divide the difference between the second known TDS level (3430 ppm) and the first known TDS level (918 ppm) by the difference between the second known mV level (1960.93) and the first known mV level (545.79). The system control unit 620 will use substitution to define b for the above formula by using the second known TDS level (3430 ppm) as X, the second known mV level (1960.93) as Y, and m as defined above.

The conductivity of the aqueous liquid is proportional to the conductivity so that an increase in current is indicative of an increase in total dissolved solids (TDS).

In one embodiment, ORP sensors are only checked for sufficient span using a quinhydrone solution mixed with two different pH buffers. Since ORP sensors do not necessarily need calibration, ORP sensor calibration memory 618C is optional. Even without calibration information, the ORP sensor calibration memory 618C is useful for providing identity and tracking information for each ORP sensor.

Each time a sensor is connected, the microprocessor of the controller 620 detects the presence of the sensor through the 1 wire interface. It then is queried for the calibration information which is compared to the calibration file held in its own internal flash memory. If it is the same no action is taken. If it is different, it prompts to overwrite the previous record.

The sensor 612 can be configured for use with a Hayward Sense and Dispense system, which uses a salt chlorine supplier which generates chlorine by placing a DC current across two electrodes which separates the chlorine from the sodium chloride (NaCl). The chlorine supplier is controlled by the ORP sensor. The pH is controlled by monitoring the pH with a probe based on standard pH probe construction and actuating a valve on an acid tank to inject the proper amount of acid to maintain the pH at the desired level. Since the action of the chlorine supplier raises the pH over time, there is a need for addition of acid to keep the pH in bounds.

In one form, the sensors 612 supplant sensors currently in use along with the attendant hardware and software to provide more accuracy and longevity.

Adjustment of Levels

In one form, controller 620 stores a given amount of chemicals needed to change either the pH level or ORP level of the water to a desired level. Various automated chemical dispensing systems to adjust pH/ORP are provided, for example, by Hayward Industries Inc. (Elizabeth, N.J.). Hayward Sense and Dispense® technology provides chemistry kits for sampling pH and free chlorine levels and adjusting chemical feeding. The Sense and Dispense® system uses a proportional feed algorithm that continuously tests the water, samples pH and sanitizing activity, and adjusts chemical feeding on a basis proportional to the demand.

Sense and Dispense® consists of two kits. The first is AQL-CHEM, a pH and ORP sensing kit which uses a chlorine generator to increase the level of free chlorine. The chlorine generator, also known as salt cell, salt generator, or salt chlorine supplier, uses electrolysis in the presence of dissolved salt (NaCl) to produce hypochlorous acid (HOCl) and sodium hypochlorite (NaOCl), which are the sanitizing agents commonly used in swimming pools.

The adjustment of pH can be achieved using a second kit, AQL-CHEM2, which includes a manifold that connects to a carbon dioxide ($CO_2$) tank to inject carbon dioxide into the pool water. Carbon dioxide reduces pH to recommended levels by forming carbonic acid ($H_2CO_3$), a weak acid that will lower the pH of the pool water slowly without the safety or health concerns normally associated with stronger acids.

As an alternative to carbon dioxide, the Sense and Dispense® system also supports commercially available peristaltic acid pumps. With AQL-CHEM3, a Stenner Pump acid connected to a 15 gallon tank lowers the pool water pH by introduction of muriatic acid (aqueous hydrochloric acid).

FIG. 7 is a perspective view of a sensor according to one embodiment of the invention. FIG. 8 is cross-sectional view taken along lines 8-8 of FIG. 9. FIG. 9 is cross-sectional view taken along lines 9-9 of FIG. 7. The sensor 612 includes an anode 702 sealed in a tube 703 comprising a proton exchange membrane such as a copolymer of tetrafluoroethylene (e.g., a Nafion™ tube) and a cathode 704 spaced from the anode 702. The anode 702 and cathode 704 are supported by and wrapped over a wall 706 of an insulative housing 708 with sealing gasket 709 (e.g., an o-ring) which also supports a temperature sensing device such as a thermistor 710 having a resistance which varies with temperature. Thermistor electrodes TH1 and TH2 are connected to the thermistor 710 and to the system control unit 620 via a wire harness (not shown). In one embodiment, the thermistor 710 has a small amount of current running through it, e.g., a bias current, which is sent by the system control unit 620. The system control unit 620 converts resistance changes to voltage changes by using a current source to apply a bias current across the thermistor to produce a control voltage. It is contemplated that thermistor 710 can be any temperature sensing device providing a signal indicative of the temperature of the device.

A printed circuit board 712 has twelve plated through holes connected to a circuit printed on a surface of the board 712. Six plated through holes in the board 712 receive and electrically connect to one end of six wires 714; the other end of the wires connect to the electrical connector block of the circuits illustrated in FIGS. 2-5. The electrical connector block is connected to system control unit 114, 620 (shown in FIGS. 1 and 6) by a wire harness (not shown). In FIG. 8, only three wires 714A, 714B, 714C of the six wires 714 are illustrated.

Two plated through holes in the board 712 receive and electrically connect to electrodes (not shown) of the calibration memory device 618 which is mounted on the board 712. Two plated through holes in the board 712 receive and electrically connect to the thermistor electrodes TH1 and TH2. Two plated through holes in the board 712 receive and electrically connect to the anode 702 and cathode 704. Thus, the six wires 714 are connected to the calibration memory device 618, the thermistor electrodes TH1, TH2, and to the anode 702 and cathode 704 via the circuit printed on the surface of the board 712.

In one form, the sensor 612 comprises a chlorine sensor comprising a gold cathode 704 and a platinum anode 702 sealed within a tube comprising a proton exchange membrane such as a copolymer of tetrafluoroethylene. The tube provides a barrier to oxygen and anions from the environment exterior to the tube except as may pass through the tube. A voltage source is configured for applying a bias voltage (e.g., 350 millivolts) between the anode and the cathode, wherein a positive voltage is applied to the anode and a negative voltage is applied to the cathode. The chlorine sensor output is a current signal which is indicative of the free chlorine in the aqueous liquid. The current signal is temperature dependent so that the EEPROM provides to the system control unit the necessary information to calibrate the current signal based on the temperature of the aqueous liquid.

In one form, the sensor 612 comprises a thermistor 720 and a pH sensor comprising: (i) a gel-filled reference electrode (e.g., anode 704); and (ii) a sensing electrode (e.g., cathode 702) of antimony/antimony oxide or bismuth/bismuth oxide having an electroactive surface sealed within a tube comprising a proton exchange membrane such as a copolymer of tetrafluoroethylene that provides a barrier for the sensing electrode to both oxygen and anions from the environment exterior to the tube. The pH sensor output is a current signal which is indicative of the pH of the aqueous liquid. The current signal is temperature dependent so that the EEPROM provides to the system control unit the necessary information to calibrate the current signal based on the temperature of the aqueous liquid.

In one form, the sensor 612 comprises a thermistor 720 and a halogen sensor such as a chlorine sensor comprising a metal anode 702 shielded by a low electrical resistance, water-permeable, oxygen barrier comprising a tube comprising a proton exchange membrane such as a copolymer of tetrafluoroethylene that provides a barrier for the sensing electrode to both oxygen and anions from the environment exterior to the tube. A voltage source is configured for applying a bias voltage (e.g., 350 millivolts) between the anode and the cathode, wherein a positive voltage is applied to the anode and a negative voltage is applied to the cathode. The halogen sensor output is a current signal which is indicative of the halogen in the aqueous liquid. The current signal is temperature dependent so that the EEPROM provides to the system control unit the necessary information to calibrate the current signal based on the temperature of the aqueous liquid.

In one form, the sensor 612 comprises a total dissolved solids (TDS) sensor comprising a pair of spaced-apart electrodes configured to be excited by a sine wave voltage of 16 kHz at 1V AC excitation voltage. A current amplifier and rectifier electrically responsive to the pair of spaced-apart electrodes generate a voltage indicative of the voltage between the spaced-apart electrodes. A converter electrically responsive to the voltage indicative of the voltage between the spaced-apart electrodes converts the indicative voltage for at least one of display and processing. A display electrically responsive to the converter displays a total dissolved solids measurement in the aqueous solution in which the pair of spaced apart electrodes is placed. The TDS sensor output is a current signal which is indicative of the TDS of the aqueous liquid. The TDS of the aqueous liquid is proportional to its conductivity so that an increase in current is indicative of an increase in total dissolved solids (TDS).

The current signal indicating TDS is generally insensitive to temperature for aqueous liquids so the EEPROM provides other information such as device identification (ID) and/or a serial number. In the event that the current signal is temperature dependent for the TDS of a particular fluid being sensed, the TDS sensor can include a thermistor 710 and the EEPROM provides to the system control unit the necessary information to calibrate the current signal based on the temperature of the aqueous liquid.

In one form, the sensor 612 comprises an ORP sensor comprising a gold cathode 704 and a platinum anode 702 sealed within a tube comprising a proton exchange membrane such as a copolymer of tetrafluoroethylene. The tube provides a barrier to oxygen and anions from the environment exterior to the tube except as may pass through the tube. The ORP sensor output is a voltage signal which is indicative of the oxidizing power of the aqueous liquid. The voltage signal is temperature dependent so that the EEPROM provides to the system control unit the necessary information to calibrate the voltage signal based on the temperature of the aqueous liquid.

Thus, the present invention comprises sensors 612, each of which is individually calibrated and has its own memory device 618 storing individualized calibration information which is unique to the individual device. In one embodiment, each sensor 612 is calibrated at a production facility before the sensor 612 is installed within a system 600 so that the calibration information stored in memory device 618 is unique to the sensor 618 and independent of any system in which the sensor 618 is installed. In one embodiment, each sensor 612 is calibrated by a reference system at a production facility before the sensor 612 is installed within a system 600 so that the calibrated sensors 618 are consistent with each other and the sensors 618 provide substantially the same output independent of the environment or system within which the sensors 618 are installed.

The Abstract and summary are provided to help the reader quickly ascertain the nature of the technical disclosure. They are submitted with the understanding that they will not be used to interpret or limit the scope or meaning of the claims. The summary is provided to introduce a selection of concepts in simplified form that are further described in the Detailed Description. The summary is not intended to identify key features or essential features of the claimed subject matter, nor is it intended to be used as an aid in determining the claimed subject matter.

For purposes of illustration, programs and other executable program components, such as the operating system, are illustrated herein as discrete blocks. It is recognized, however, that such programs and components reside at various times in different storage components of a computing device, and are executed by a data processor(s) of the device.

Although described in connection with an exemplary computing system environment, embodiments of the aspects of the invention are operational with numerous other computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of well-known computing systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the aspects of the invention may be described in the general context of data and/or processor-executable instructions, such as program modules, stored one or more tangible, non-transitory storage media and executed by one or more processors or other devices. Generally, program modules include, but are not limited to, routines, programs, objects, components, and data structures that perform particular tasks or implement particular abstract data types. Aspects of the invention may also be practiced in distributed computing environments where tasks are performed by remote processing devices that are linked through a communications network. In a distributed computing environment, program modules may be located in both local and remote storage media including memory storage devices.

In operation, processors, computers and/or servers may execute the processor-executable instructions (e.g., software, firmware, and/or hardware) such as those illustrated herein to implement aspects of the invention.

Embodiments of the aspects of the invention may be implemented with processor-executable instructions. The processor-executable instructions may be organized into one or more processor-executable components or modules on a tangible processor readable storage medium which is not a signal. Aspects of the invention may be implemented with any number and organization of such components or modules. For example, aspects of the invention are not limited to the specific processor-executable instructions or the specific components or modules illustrated in the figures and described herein. Other embodiments of the aspects of the invention may include different processor-executable instructions or components having more or less functionality than illustrated and described herein.

The order of execution or performance of the operations in embodiments of the aspects of the invention illustrated and described herein is not essential, unless otherwise specified. That is, the operations may be performed in any order, unless otherwise specified, and embodiments of the aspects of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the aspects of the invention are achieved and other advantageous results may be attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the aspects of the invention by way of example and not by way of limitation. This description enables one skilled in the art to make and use the aspects of the invention, and describes several embodiments, adaptations, variations, alternatives and uses of the aspects of the invention, including what is presently believed to be the best mode of carrying out the aspects of the invention. Additionally, it is to be understood that the aspects of the invention is not limited in its application to the details of construction and the arrangement of components set forth in the following description or illustrated in the drawings. The aspects of the invention are capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of aspects of the invention as defined in the appended claims. It is contemplated that various changes could be made in the above constructions, products, and methods without departing from the scope of aspects of the invention. In the preceding specification, various preferred embodiments have been described with reference to the accompanying drawings. It will, however, be evident that various modifications and changes may be made thereto, and additional embodiments may be implemented, without departing from the broader scope of the aspects of the invention as set forth in the claims that follow. The specification and drawings are accordingly to be regarded in an illustrative rather than restrictive sense.

What is claimed is:

1. A treatment system for treating an aqueous liquid comprising:
    a conduit for channeling the aqueous liquid to be treated;
    a treatment device in fluid communication with the conduit, the treatment device configured to supply one or more treatments to the aqueous liquid via the conduit for altering the aqueous liquid and having an input port for receiving a treatment signal indicative of an extent to which the treatment device alters the aqueous liquid;
    a sensor sensing a first parameter of the aqueous liquid and having an analog output port providing a first analog signal indicative of the sensed first parameter, said sensor sensing a second parameter of the aqueous liquid and providing a second analog signal at the analog output port indicative of the sensed second parameter, said sensor having a calibration memory device storing digital information, said digital information stored in the calibration memory device indicative of a calibration of the first parameter relative to the second parameter, and said sensor having a digital output port providing a digital signal indicative of the digital information stored in the calibration memory device; and
    a controller having a digital input port connected to the digital output port of the sensor, said controller receiving the digital signal from the sensor via the digital input port and determining a calibration of the sensor in response to the received digital signal,
    said controller having an analog input port connected to the analog output port of the sensor, said controller receiving the first and second analog signals via the analog input port and determining an adjusted first parameter of the aqueous liquid relative to the second parameter based on the received analog signals and based on the calibration of the sensor,
    said controller having an output port connected to the treatment device providing the treatment signal to the input port of the treatment device, said treatment device responsive to the treatment signal and configured to control the extent to which the treatment device alters the aqueous liquid as a function of the determined adjusted first parameter.

2. The treatment system of claim 1 wherein the sensor comprises at least one of:
    (a) a chlorine sensor so the first parameter is current signal indicative of a free chlorine of the aqueous liquid,
    (b) an ORP sensor so that the first parameter is a voltage signal indicative of free chlorine of the aqueous liquid, or
    (c) a pH sensor so that the first parameter is current signal indicative of a pH of the aqueous liquid; and
    wherein the sensor further comprises a temperature sensing device so that the second parameter is a signal indicative of a temperature of the aqueous liquid.

3. The treatment system of claim 2 wherein the sensor comprises a thermistor so that the second parameter is a signal indicative of a resistance of the thermistor which is indicative of a temperature of the aqueous liquid.

4. A sensing device comprising a sensor configured to sense a first parameter and a second parameter of a liquid and having an analog output port configured to provide a first analog signal indicative of the sensed first parameter and configured to provide a second analog signal indicative of the sensed second parameter, said sensor having a calibration memory device storing individualized digital information specific to the calibration memory, said individualized digital information stored in the calibration memory device indicative of a calibration of the first parameter relative to the second parameter, and said sensor having a digital output port providing a digital signal indicative of the individualized digital information stored in the calibration memory device.

5. The device of claim 4 in combination with a treatment system for treating an aqueous liquid, said treatment system comprising:
    a conduit for channeling the aqueous liquid to be treated;
    a treatment device associated with the conduit for altering the aqueous liquid and having an input port for receiving a treatment signal indicative of an extent to which the treatment device alters the aqueous liquid; and
    a controller having a digital input port connected to the digital output port of the sensor, said controller receiving the digital signal via the digital input port and determining a calibration of the sensor,
    said controller having an analog input port connected to the analog output port of the sensor, said controller receiving the analog signals via the analog input port and determining the first parameter relative to the second parameter based on the received analog signals and based on the calibration of the sensor,
    said controller having an output port connected to the treatment device providing the treatment signal to the input port of the treatment device, said treatment signal configured to control the treatment device as a function of the determined parameter by controlling the extent to which the treatment device alters the aqueous liquid.

6. The device of claim 4 wherein the liquid is an aqueous liquid and wherein the sensor comprises a thermistor sensing temperature providing the second analog signal and a chlorine sensor providing the first analog signal comprising a gold cathode and a platinum anode, the platinum anode being sealed within a tube comprising a proton exchange membrane, wherein the tube provides a barrier to oxygen and anions from the environment exterior to the tube except as may pass through the tube.

7. The device of claim 4 wherein the liquid is an aqueous liquid and wherein the sensor comprises a thermistor sensing temperature providing the second analog signal and a pH sensor providing the first analog signal comprising:
    (i) a gel-filled reference electrode; and
    (ii) a sensing electrode of antimony/antimony oxide or bismuth/bismuth oxide having an electroactive surface sealed within a tube comprising a proton exchange membrane that provides a barrier for the sensing electrode to both oxygen and anions from the environment exterior to the tube.

8. The device of claim 4 wherein the liquid is an aqueous liquid and wherein the sensor comprises a thermistor sensing temperature providing the second analog signal and a halogen sensor providing the first analog signal comprising a metal anode shielded by a low electrical resistance, water-permeable, oxygen barrier comprising a tube comprising a proton exchange membrane that provides a barrier to both oxygen and anions from the environment exterior to the tube.

9. The device of claim 4 wherein the liquid is an aqueous liquid and wherein the sensor comprises a total dissolved solids (TDS) sensor comprising: a pair of spaced-apart electrodes configured to be excited by a sine wave voltage; a current amplifier and rectifier electrically responsive to the pair of spaced-apart electrodes configured to generate a voltage indicative of the voltage between the spaced-apart electrodes; a converter electrically responsive to the voltage indicative of the voltage between the spaced-apart electrodes configured to convert the indicative voltage for at least one of display and processing; a display electrically responsive to the converter configured to display a total dissolved solids measurement in aqueous liquid in which the pair of spaced apart electrodes is placed.

10. The device of claim 4 wherein the liquid is an aqueous liquid and wherein the sensor comprises a thermistor sensing temperature providing the second analog signal and an ORP sensor providing the first analog signal comprising a gold cathode and a platinum anode, the platinum anode being sealed within a tube comprising a proton exchange membrane, wherein the tube provides a barrier to oxygen and anions from the environment exterior to the tube except as may pass through the tube.

* * * * *